US010576242B2

(12) United States Patent
Jones et al.

(10) Patent No.: US 10,576,242 B2
(45) Date of Patent: Mar. 3, 2020

(54) BI-LUMENAL TUBE CATHETER SUPPORT SYSTEM

(71) Applicant: Biosensors International Group, Ltd., Hamilton (BM)

(72) Inventors: Eric Jones, Livermore, CA (US); Eugene Serina, Fremont, CA (US); Roseann Ward, Fremont, CA (US); Emilio Crisolo, Union City, CA (US)

(73) Assignee: Biosensors International Group, Ltd., Hamilton (BM)

( * ) Notice: Subject to any disclaimer, the term of this patent is extended or adjusted under 35 U.S.C. 154(b) by 154 days.

(21) Appl. No.: 15/578,107

(22) PCT Filed: May 27, 2016

(86) PCT No.: PCT/US2016/034818
§ 371 (c)(1),
(2) Date: Nov. 29, 2017

(87) PCT Pub. No.: WO2016/196364
PCT Pub. Date: Dec. 8, 2016

(65) Prior Publication Data
US 2018/0154109 A1 Jun. 7, 2018

Related U.S. Application Data

(60) Provisional application No. 62/168,580, filed on May 29, 2015.

(51) Int. Cl.
A61M 25/00 (2006.01)
A61M 25/01 (2006.01)
(Continued)

(52) U.S. Cl.
CPC .... *A61M 25/0029* (2013.01); *A61M 25/0097* (2013.01); *A61M 25/0136* (2013.01);
(Continued)

(58) Field of Classification Search
CPC .......... A61M 25/0026; A61M 25/0028; A61M 25/0029; A61M 25/0097; A61M 25/0136;
(Continued)

(56) References Cited

U.S. PATENT DOCUMENTS 8,747,350 B2 6/2014 Chin et al.
8,834,510 B2 9/2014 Wilson et al.
(Continued)

OTHER PUBLICATIONS

PCT/US2016/034818 , "International Preliminary Report on Patentability", dated Dec. 14, 2017, 5 pages.
(Continued)

*Primary Examiner* — Jocelin C Tanner
(74) *Attorney, Agent, or Firm* — Kilpatrick Townsend & Stockton LLP

(57) ABSTRACT

A catheter having a multilumenal tube surrounded by a slotted hypotube is provided. The catheter has a tube holder that houses the multilumenal tubing and slidably engages the hypotube, and has internal passages configured to receive one of more tubes from the multilumenal tube. The multilumenal tubing separates into one or more tubings, each comprising a lumen, such that the tubings exit the tube holder at different locations. The slotted hypotube slidably engages a key in the tube holder that prevents the multilumenal tubing from rotating relative to the tube holder and the one of more tubings that separate from the multilumenal tubing. Advantages provided by the slotted hypotube/tube holder assembly are described.

24 Claims, 6 Drawing Sheets

(51) Int. Cl.
*A61M 25/09* (2006.01)
*A61M 29/02* (2006.01)

(52) U.S. Cl.
CPC ............ *A61M 25/09* (2013.01); *A61M 29/02* (2013.01); *A61M 25/0026* (2013.01); *A61M 25/0028* (2013.01); *A61M 2025/0004* (2013.01); *A61M 2025/0006* (2013.01); *A61M 2025/0175* (2013.01)

(58) Field of Classification Search
CPC .................. A61M 25/09; A61M 29/02; A61M 2025/0004; A61M 2025/0006; A61M 2025/0175
See application file for complete search history.

(56) References Cited

U.S. PATENT DOCUMENTS

| | | |
|---|---|---|
| 2003/0078537 A1 | 4/2003 | Jang |
| 2005/0059958 A1 | 3/2005 | Lessard et al. |
| 2005/0070847 A1 | 3/2005 | Van Erp et al. |
| 2005/0080398 A1 | 4/2005 | Markel et al. |
| 2005/0234499 A1 | 10/2005 | Olson et al. |
| 2014/0031843 A1 | 1/2014 | Rottenberg et al. |

OTHER PUBLICATIONS

PCT/US2016/034818 , "International Search Report and Written Opinion", dated Aug. 8, 2016, 6 pages.
EP16804167.1 , "Extended European Search Report", dated Jan. 18, 2019, 10 pages.

BI-LUMENAL TUBE CATHETER SUPPORT SYSTEM

CROSS-REFERENCES TO RELATED APPLICATIONS

This application claims the benefit of priority to U.S. Provisional Patent Application No. 62/168,580, filed May 29, 2015, which is incorporated by reference herein in its entirety.

BACKGROUND OF THE INVENTION

The present disclosure describes a catheter useful for treating a vessel of a subject. The catheter comprises an outer sheath that surrounds a multilumenal tubing. The catheter further comprises a slotted hypotube that at least partially surrounds the multilumenal tubing. A tube holder houses the multilumenal tubing, and the slotted hypotube is configured to slide within internal passages or channels within the tube holder, such that the hypotube slides relative to both the tube holder and the multilumenal tubing. The slotted hypotube combined with the tube holder provides advantages over existing catheters further described herein.

BRIEF SUMMARY OF THE INVENTION

Described herein is a catheter comprising an outer sheath surrounding a multilumenal tubing. The catheter can be used for treating vascular lesions. For example, the catheter can be a balloon catheter that is useful for expanding the diameter of a blood vessel that is narrowed by arteriosclerosis. In one aspect, the proximal end region of the outer sheath is connected to a hypotube that surrounds the multilumenal tubing, and the hypotube is configured to slide in a proximal to distal direction relative to the multilumenal tubing. In some embodiments, the catheter comprises a multi-lumenal tubing surrounded by a slidable hypotube, and the hypotube has a longitudinal slot. The longitudinal slot is configured to allow a tube that separates from the multilumenal tubing to pass through the slot. In some embodiments, the catheter comprises a tube holder located near the proximal end that houses the multilumenal tubing. In some embodiments, the tube holder is located where the multilumenal tubing separates into at least a first and second tubing. The multilumenal tubing can separate into at least a first tubing that passes through the longitudinal slot in the hypotube and exits the tube holder at a first location, and at least a second tubing that exits the tube holder at a second location. In some embodiments, the tube holder comprises internal passages dimensioned to accept the combined multilumenal tubing that is surrounded by the hypotube and the separated first and second tubings. The tube holder can comprise a key within the passage dimensioned to accept the combined multilumenal tubing, such that the key engages the slot and prevents the hypotube from rotating at the position where the multilumenal tubing separates into the first and second tubing, while allowing the hypotube to slide within the passage dimensioned to accept the combined multi-lumenal tubing. Thus, the slotted hypotube combined with the tube holder described herein provides unexpected advantages, including (i) allowing the first tubing to separate from the multilumenal tubing at a distal location, and (ii) preventing rotation of the hypotube, which could otherwise rotate and cut the first lumen tubing.

In some embodiments, the first location where the first tubing exits the tube holder is located distal to the second location where the second tubing exits the tube holder. For example, the second location can be located at a proximal end portion of the tube holder. In some embodiments, the internal passages of the tube holder are connected to each other at a junction, for example, a Y-shaped junction. The key can be attached to the tube holder distally of the junction, and the hypotube can surround the second tubing proximal to the junction.

In some embodiments, the hypotube comprises a longitudinal axis and the longitudinal slot extends at least partially along the longitudinal axis. For example, the longitudinal slot can extend from a proximal end to a distal end of the hypotube. In some embodiments, the hypotube slidably extends through the tube holder in a proximal to distal direction in the internal passage that extends in a proximal direction from the junction. In some embodiments, the internal passage that extends in a proximal direction from the junction comprises the second tubing.

In some embodiments, the hypotube is C-shaped in cross-section, and the key engages the open end of the "C." The key functions to prevent the hypotube from rotating in a circumferential direction. In some embodiments, the catheter further comprises a second key attached to the tube holder that is configured to slidably engage the longitudinal slot of the hypotube. For example, the second key can be attached to the tube holder at the second location where the second tubing exits the tube holder. The second key can also engage the longitudinal slot to prevent the hypotube from rotating relative to the multilumenal tubing. Thus, in some embodiments, the longitudinal slot of the hypotube slidably engages the first and second keys.

In some embodiments, the hypotube comprises a plurality of circumferential slots that extend partially around the circumference of the hyptotube. The circumferential slots provide flexibility to help prevent the hypotube from kinking. The hypotube can be made of metal or plastic.

In some embodiments, the first tubing comprises a guide wire lumen and the second tubing comprises an inflation lumen. The multilumenal tubing can be a coaxial tube such that the guide wire lumen tubing is surrounded by the inflation lumen tubing. The guide wire lumen is configured to slidably receive a guide wire that extends through the guide wire lumen.

In some embodiments, the tube holder is disposed within a handle located near the proximal end of the catheter. In some embodiments, the first tubing exits the handle at a first location, the second tubing exits the handle at a second location, and the first location is located distally relative to the second location.

Further embodiments will now be described.

BRIEF DESCRIPTION OF THE DRAWINGS

FIG. 2A shows an isometric view. FIG. 2B shows an end view.

DEFINITIONS

Figure 1A:
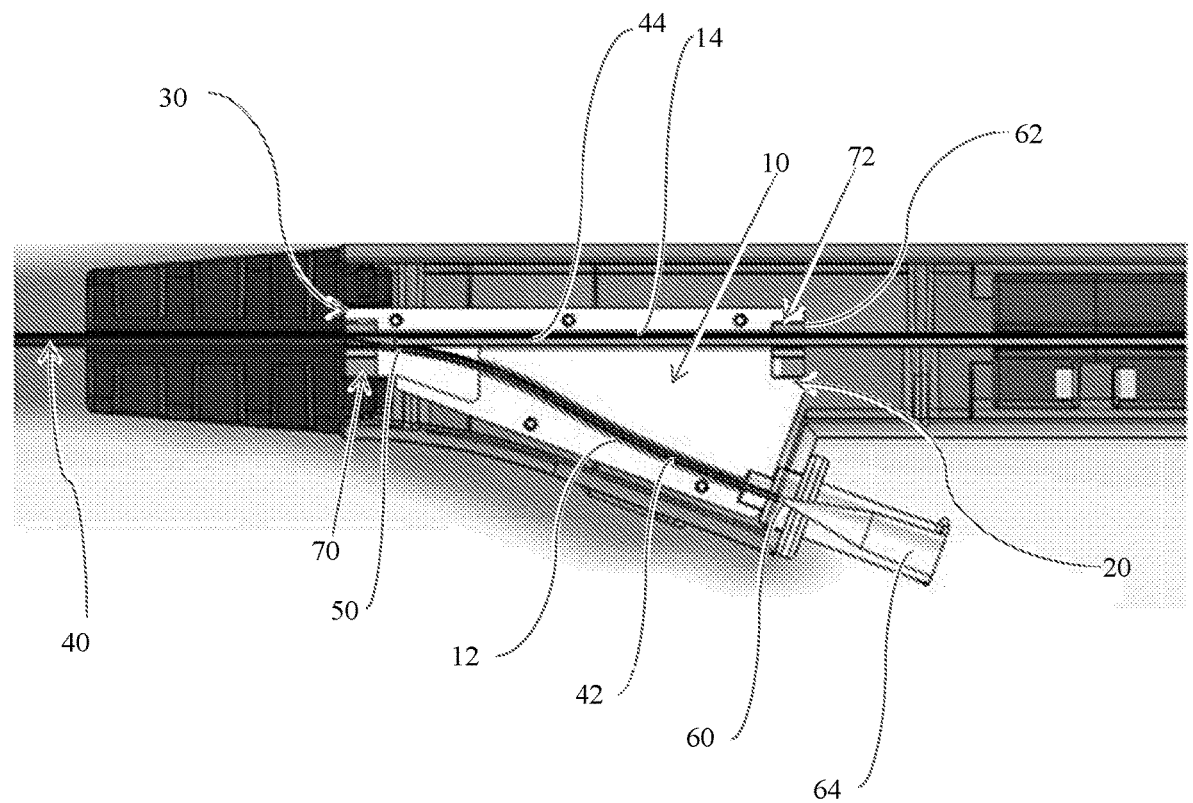
FIG. 1A shows a cut-away (sectional) side view of one embodiment of a tube holder described herein.

Unless defined otherwise, technical and scientific terms used herein have the same meaning as commonly understood by a person of ordinary skill in the art. The term "a" or "an" is intended to mean "one or more." The term "comprise" and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The term "about," when modifying any amount, refers to the variation in that amount typically encountered by one of skill in the art, i.e., in the field of angioplasty catheter design. For example, the term "about" refers to the normal variation encountered in measurements for a given analytical technique, both within and between batches or samples. Thus, the term about can include variation of 1-10% of the measured amount or value, such as +/−1%, 2%, 3%, 4%, 5%, 6%, 7%, 8%, 9% or 10% variation. The amounts disclosed herein include equivalents to those amounts, including amounts modified or not modified by the term "about."

The term "multilumenal tubing" refers to a tube having two or more lumens, such as two, three, four or more lumens. In some embodiments, the multilumenal tubing is a coaxial tube comprising a first inner tubing surrounded by a second outer tubing, where each tubing has a lumen such that the first tubing is disposed within the lumen of the second tubing.

The term "hypotube" refers to an elongate tubular member having an inside diameter that is capable of slidably receiving another tube or shaft. The hypotube is typically cylindrical in shape having a longitudinal axis, a radial axis, and a lumen. Hypotubes can be manufactured from metals such as stainless steel or nitinol. In some embodiments, the hypotube is made of plastic.

The term "slotted hypotube" refers to a hypotube having a longitudinal slot that extends at least partly along the length or longitudinal axis of the hypotube. The slot comprises an elongate opening that is continuous with the lumen of the hypotube and extends partially around the circumference of the hypotube. In some embodiments, the slot is dimensioned such that a tube can exit the hypotube through the slot.

The terms "proximal" and "distal," when used to describe a catheter, refer to directions towards and away from the cardiologist controlling the catheter, respectively. For example, the tube holder or handle of the catheter described herein is located near the proximal end, and an angioplasty balloon or cardiovascular stent carried by the catheter is typically located at or near the distal end of the catheter. When referring to vascular vessels within the body of a subject, the term "distal" means towards the heart, and "proximal" means away from the heart.

The term "multilumenal tubing" refers to a tube having multiple lumens. Each lumen can be separated from other lumens by a partition or wall that extends along the longitudinal axis of the tubing. In some embodiments, each lumen is surrounded by a flexible tube. In some embodiments, the tubes are concentric tubes, where one tube is located inside another tube, such as, for example, a coaxial tube. In some embodiments, the tubes are not concentric or coaxial tubes.

The term "combined multilumenal tubing" refers to a multilumenal tube that is not separated into individual tubings that surround a lumen. For example, the term refers to the multilumenal tubing that is distal to the point of separation of the tubings in the tube holder.

DETAILED DESCRIPTION OF THE INVENTION

Described herein is a catheter comprising a multilumenal tubing that is surrounded or covered by an outer sheath, and the multilumenal tubing is at least partially surrounded by a slotted hypotube near the proximal end. The catheter further comprises a tube holder configured to house the multilumenal tubing and the slotted hypotube. The slotted hypotube is configured to slide relative to both the tube holder and the multilumenal tubing. The tube holder is further configured to allow the multilumenal tubing to separate into one or more tubings comprising a lumen, such that the tubings exit the tube holder at different locations. For example, a first tubing can separate from the combined multilumenal tubing at a distal end portion of the tube holder, which provides the advantage that the length of the lumen is shorter than if the first tubing separated from the combined multilumenal tubing at a proximal end of the tube holder. To allow for the first tubing to exit at the distal end portion of the tube holder, the outer sheath comprises a longitudinal slot that runs parallel to the tubing lumen. The slotted hypotube slidably surrounds the combined multilumenal tubing at the point where the first tubing separates from the multilumenal tubing with the slot oriented to allow the first tubing to pass through easily. The slotted hypotube slidably engages a key in the tube holder that prevents the multilumenal tubing from rotating relative to the tube holder and first tubing. Thus, the slotted hypotube combined with the tube holder described herein provides the advantages of (i) allowing the first tubing to separate from the multilumenal tubing at a distal location, and (ii) preventing rotation of the hypotube, which could otherwise rotate and sever the first lumen tubing.

The hypotube described herein is configured to be slidable relative to the multilumenal tubing, such that the hypotube can slide in a proximal to distal direction (and vice versa, i.e., in a distal to proximal direction) over the external surface of the multilumenal tubing. The hypotube comprises a longitudinal slot that allows at least one tube of the multilumenal tubing to exit the hypotube. For example, at least a first tubing can exit the hypotube by passing through the longitudinal slot in the hypotube. The first tubing then exits the tube holder at a first location. The multilumenal tubing can further separate into at least a second tubing that exits the tube holder at a second location. In some embodiments, the first location is distal to the second location. In some embodiments, the second location is located at or near a proximal end portion of the tube holder.

The multilumenal tubing can comprise at least a guide wire lumen and an inflation lumen. In some embodiments, the first tubing comprises a guide wire lumen and the second tubing comprises an inflation lumen. In some embodiments, the multilumenal tubing is a coaxial tube. In some embodiments, the tubing comprising the guide wire lumen is surrounded by the tubing comprising the inflation lumen. In some embodiments, the catheter comprises a guide wire extending through the guide wire lumen.

The tube holder comprises internal passages or channels that are dimensioned or configured to accept the multilumenal tubing surrounded by the hypotube. The tube holder can also comprise internal passages that are dimensioned to slidably receive the tubings (e.g., the guide wire tubing and inflation tubing) that are separated from the combined multilumenal tubing. The internal passages of the tube holder are connected to each other at a junction. In one embodiment, the junction is a Y-shaped junction. In some embodiments, the internal passage of the tube holder proximal to the junction is dimensioned to accept the second (e.g., inflation lumen) tubing, which surrounds a closed lumen. In some embodiments, the hypotube slidably surrounds the second (e.g., inflation lumen) tubing proximal to the junction. In some embodiments, the internal passage extending in a proximal direction from the junction is configured to slidably receive the hypotube such that the hypotube can slidably extend through the tube holder in a proximal to distal direction (and vice versa, i.e., in a distal to proximal direction). Thus, the internal passage of the tube holder can be dimensioned to accept the hypotube that slidably surrounds the second tubing and lumen. In some embodiments, the internal passage(s) of the tube holder surround a closed lumen.

In some embodiments, the tube holder comprises a first key within the internal passage dimensioned to accept the combined multilumenal tubing. The key is configured to slidably engage the longitudinal slot of the hypotube and thereby prevent the hypotube from rotating in a circumferential direction (i.e., about its longitudinal axis) at the position where the combined multilumenal tubing separates into at least the first and second tubings. In some embodiments, the hypotube is "C"-shaped in cross section, such that key engages the open end of the "C" and prevents the hypotube from rotating in a circumferential direction. The key is further configured to allow the hypotube to slide within the internal passages of the tube holder, for example, within an internal passage configured to accept the combined multilumenal tubing.

The first key is attached to the tube holder distally of the junction where the internal passages connect to each other. The tube holder can further comprise a second key that is configured to slidably engage the longitudinal slot of the hypotube and thereby help prevent the hypotube from rotating in a circumferential direction. The second key can engage the longitudinal slot of the hypotube to help prevent the hypotube from rotating relative to the multilumenal tubing. In some embodiments, the second key is attached to the tube holder at the location where the second tubing exits the tube holder. In some embodiments, the second key is attached to the proximal end portion of the tube holder. To provide additional anti-rotation stability, the longitudinal slot of the hypotube can slidably engage the first and second keys.

In some embodiments, the hypotube comprises a longitudinal axis and the longitudinal slot extends at least partially along the longitudinal axis. The longitudinal slot can extend from the proximal end to the distal end of the hypotube. In some embodiments, the hypotube comprises a plurality of circumferential slots that extend partially around the circumference of the hypotube. The circumferential slots add flexibility and help prevent buckling of the hypotube. In some embodiments, the circumferential slots are oriented perpendicular or substantially perpendicular to the longitudinal axis of the hypotube. In some embodiments, the width of the slots along the longitudinal axis is substantially the same. In some embodiments, the width of the slots along the longitudinal axis is not uniform, such that some slots are wider than other slots in the proximal-to-distal direction. In some embodiments, the hypotube is made of metal or plastic.

In some embodiments, the proximal end region of the outer sheath is bonded to the slotted hypotube. Alternatively, in some embodiments, the proximal end region of the outer sheath comprises a slot to allow the exit of one or more tubings, such as the guide wire lumen tubing. In this embodiment, the outer sheath slidably covers the slotted hypotube such that the slot in the sheath aligns with the slot in the hypotube. In another embodiment, the proximal end region of outer sheath is slotted and performs the function of the slotted hypotube. In this embodiment, the outer sheath is constructed of a rigid material that resists kinking and buckling, and can comprise circumferential slots that add flexibility.

The catheter can comprise a system including the tube holder and a handle located near the proximal end of the catheter. In some embodiments, the handle comprises a sliding mechanism that is attached to the proximal end portion of the hypotube. In some embodiments, the sliding mechanism is coupled to the outer sheath of the catheter, and can be used to retract and/or advance the outer sheath relative to a balloon or stent disposed at the distal end portion of the catheter. The handle can further comprise a stress relief structure made of a flexible thermoplastic elastomer located proximal to the tube holder. In some embodiments, the handle comprises one or more ports connected or attached to one or more tubings of the multilumenal tubing. In some embodiments, the handle comprises one or more ports in fluid connection with one or more tubings of the multilumenal tubing. It will be understood that the term "fluid" can refer to a liquid or air. In some embodiments, a first port is in fluid connection with the first tubing that exits the tube holder at the first location. In some embodiments, a second port is in fluid connection with the second tubing that exits the tube holder at the second location. In one embodiment, the second port is in fluid connection with the inflation lumen tubing. In some embodiments, the second port is located at the proximal end portion of the handle. In some embodiments, the first port is located distal of the second location on the handle. In some embodiments, the first port is configured to accept the first tubing comprising a guide-wire lumen. In some embodiments, the one or more ports comprise Luer fittings.

The catheter described herein is useful for performing angioplasty procedures or delivering a device, such as a stent, to a vascular vessel of a subject. The catheter can also be used to treat or otherwise manipulate other internal vessels or tubes in a subject, such as the urethra. In some embodiments, the catheter is a balloon catheter.

Specific non-limiting embodiments will now be described.

Referring now to FIG. 1, a cut-away view of an illustrative tube holder will be described. As shown in FIG. 1A, the tube holder (10) (also referred to as a "clamshell") comprises a proximal end (20) and a distal end (30). The tube holder is connected to the multilumenal tubing (40), which enters the tube holder at the distal end (30). In some embodiments, the multilumenal tubing separates into a first tubing (42) comprising the guidewire lumen and a second tubing (44) comprising the inflation lumen at a Y-shaped junction (50). The tube holder comprises internal passages (12, 14) configured to accept the guide-wire lumen tubing and the inflation lumen tubing. The guidewire lumen tubing exits the tube holder at a first location (60), and the inflation lumen tubing exits the tube holder at a second location (62). The guidewire lumen tubing can be attached to a Luer fitting (64) that is attached to the tube holder.

The tube holder (10) further comprises at least a first collar (70) located at the distal end of the tube holder, just distal of the Y-shaped junction (50). The collar (70) comprises a key (shown in FIG. 2) that is slidably engaged with a slotted hypotube (shown in FIG. 4). The tube holder can further comprise a second collar (72) located at the proximal end of internal passage (14). The collar (72) can also comprise a key that is slidably engaged with the slotted hypotube. In some embodiments, the first and second collars are substantially the same.

Figure 1B:
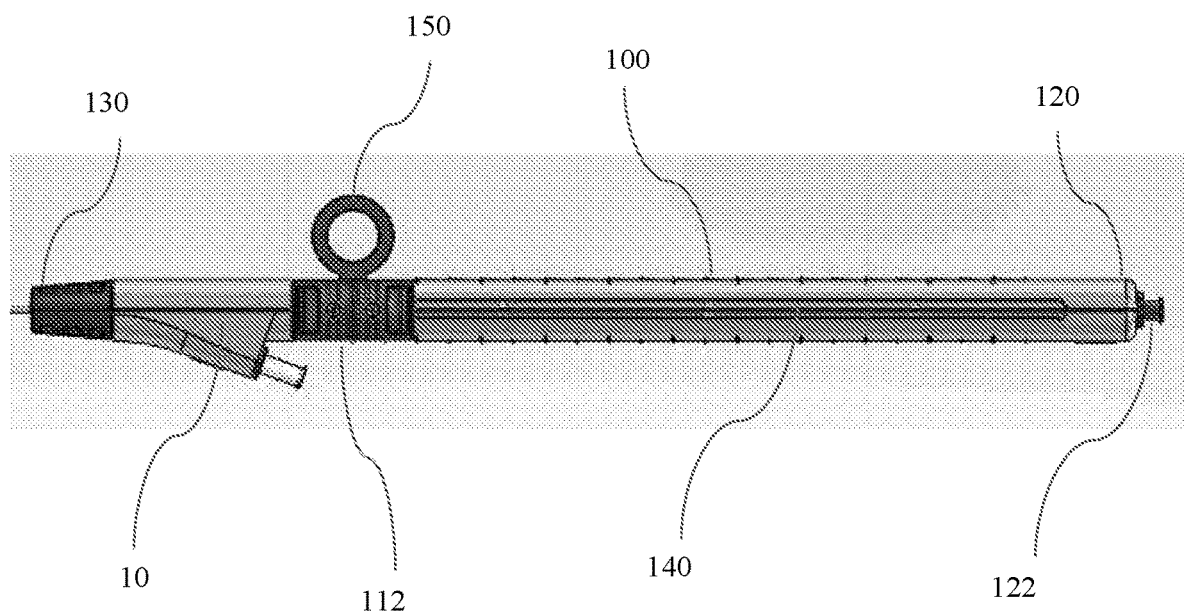
FIG. 1B shows an external side view of one embodiment of a handle for a catheter described herein.

As shown in FIG. 1B, the tube holder (10) can be disposed within a handle (100). The handle comprises a proximal end (120) and a distal end (130). The handle can comprise a Luer fitting (122) at the proximal end that is in fluid communication with the inflation lumen tubing. The handle comprises a slider (112) that is connected to the proximal end of the hypotube/outer sheath. The handle can also comprise a stress relief structure (140), and a safety handle (150) that is removed prior to use.

Figure 2A:
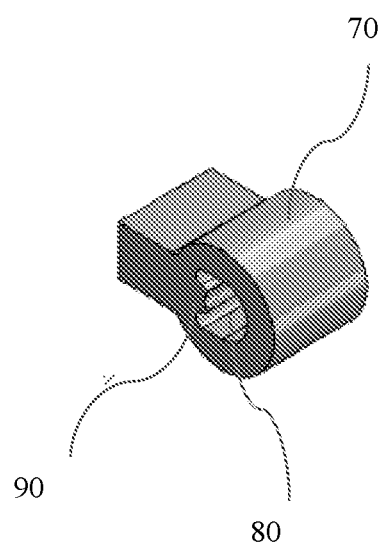
FIGS. 2A and 2B show a representative collar disposed in the "clamshell" of the handle described herein.
Figure 2B:
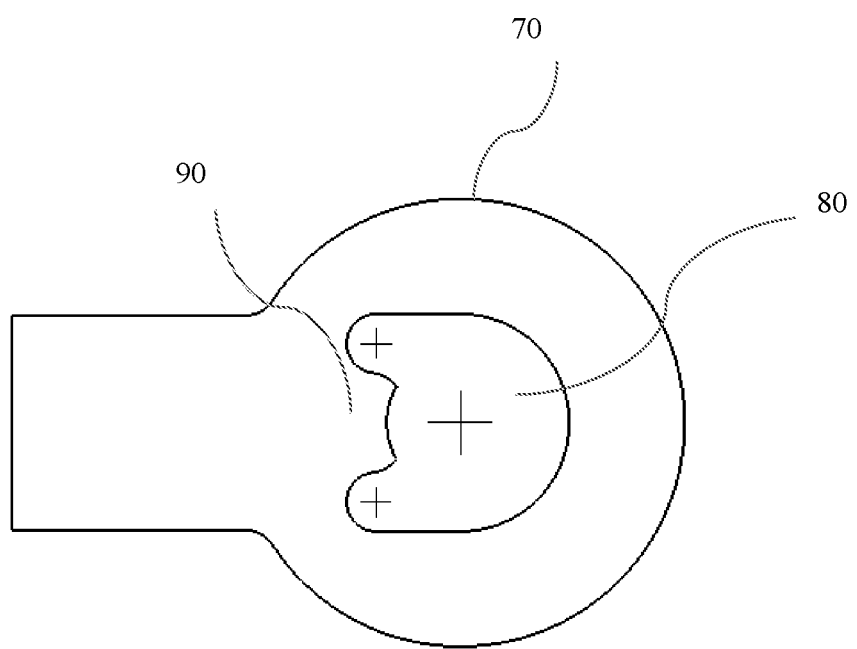

Referring now to FIG. 2, an illustrative collar assembly will now be described. FIG. 2A shows an isometric view illustrating the collar (70) having in internal passage (80) and a key (90) that extends into the interior of the passage (80). The key is configured to slidably engage the slotted hypotube described herein. FIG. 2B shows an end view of the collar assembly. In some embodiments, the collar is about 0.125 inches long. In some embodiments, the internal passage is about 0.056 to about 0.058 inches in diameter.

Figure 3:
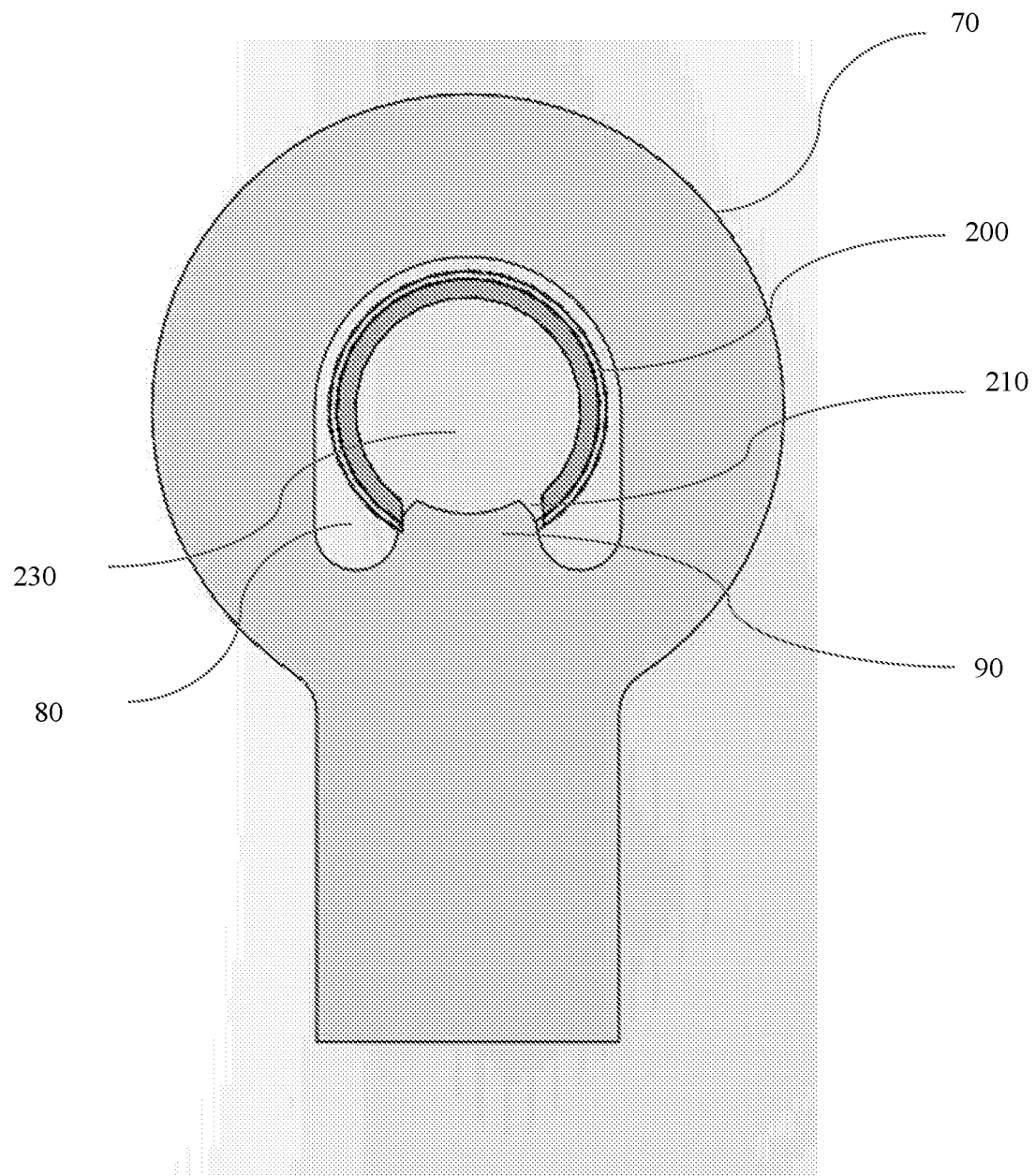
FIG. 3 shows a cross-sectional view of the collar shown in FIG. 2B in contact with a slotted hypotube described herein.

Referring now to FIG. 3, an illustrative collar assembly (70) in contact with a slotted hypotube (200) will now be described. FIG. 3 shows a cross-sectional view of the hypotube (200) having a longitudinal slot (210) that is in contact with the key (90) of the collar. The hypotube (200) is typically C-shaped, with the open end of the "C" (210) in slidable contact with the key (90). The hypotube comprises a lumen (230) that is configured to slidably receive the multilumenal tubing (40).

Figure 4:
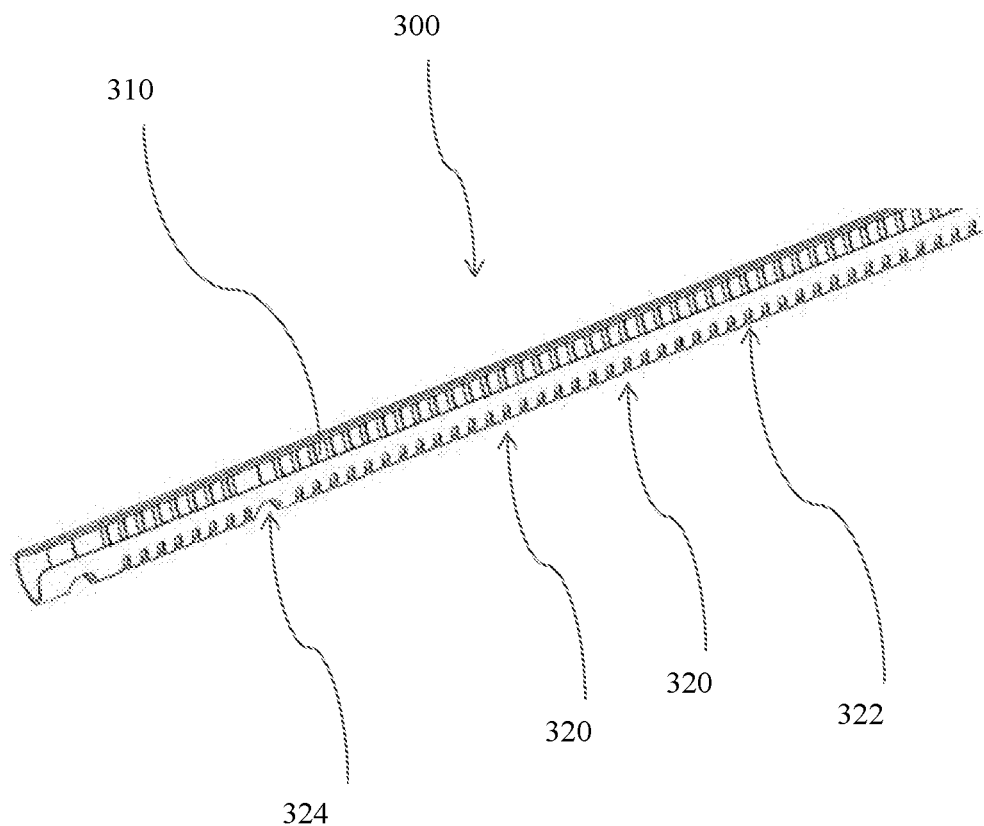
FIG. 4 shows an isometric view of a representative slotted hypotube described herein.

Referring now to FIG. 4, one embodiment of the slotted hypotube will now be described. The hypotube (300) comprises a longitudinal slot (310) that extends along the longitudinal axis. In some embodiments, the hypotube further comprises a plurality of circumferentially oriented slots (320) that extend partially around the circumference opposite the longitudinal slot. In the embodiment shown in FIG. 4, a plurality of the circumferentially oriented slots are the same width (322) along the longitudinal axis (i.e., in a proximal to distal direction), whereas some of the circumferentially oriented slots are wider (324) along the longitudinal axis and are interspersed among the other slots (322). The circumferentially oriented slots provide flexibility and prevent buckling of the hypotube. In some embodiments, the slotted hypotube is about 20 cm long.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A catheter comprising:
a multi-lumenal tubing surrounded by a slidable hypotube, the hypotube having a longitudinal slot;
a tube holder where the multi-lumenal tubing separates into at least a first tubing that passes through the longitudinal slot in the hypotube and exits the tube holder at a first location and at least a second tubing that exits the tube holder at a second location; and
where the tube holder comprises internal passages dimensioned to accept the combined multi-lumenal tubing surrounded by the hypotube and the separated first and second tubings, and
where the tube holder comprises a key within the passage dimensioned to accept the combined multi-lumenal tubing, such that the key engages the slot and prevents the hypotube from rotating at the position where the multilumenal tubing separates into the first and second tubing while allowing the hypotube to slide within the passage dimensioned to accept the combined multi-lumenal tubing.

2. The catheter of claim 1, wherein the first location is distal to the second location.

3. The catheter of claim 1, where the second location is at a proximal end portion of the tube holder.

4. The catheter of claim 1, where the internal passages are connected to each other at a junction.

5. The catheter of claim 4, where the junction is Y-shaped.

6. The catheter of claim 4, where the key is attached to the tube holder distally of the junction.

7. The catheter of claim 4, where the hypotube surrounds the second tubing proximal to the junction.

8. The catheter of claim 1, where the hypotube comprises a longitudinal axis and the longitudinal slot extends at least partially along the longitudinal axis.

9. The catheter of claim 1, wherein the longitudinal slot extends from a proximal end to a distal end of the hypotube.

10. The catheter of claim 1, where the hypotube slidably extends through the tube holder in a proximal to distal direction in the internal passage comprising the second tubing.

11. The catheter of claim 1, wherein the hypotube is C-shaped in cross-section, and the key engages an open end of the "C."

12. The catheter of claim 1, wherein the key prevents the hypotube from rotating in a circumferential direction.

13. The catheter of claim 1, further comprising a second key attached to the tube holder and configured to slidably engage the longitudinal slot of the hypotube.

14. The catheter of claim 13, where the second key is attached to the tube holder at the second location.

15. The catheter of claim 14, where the second key engages the longitudinal slot to prevent the hypotube from rotating relative to the multilumenal tubing.

16. The catheter of claim 14, where the longitudinal slot of the hypotube slidably engages the first and second keys.

17. The catheter of claim 1, wherein the hypotube comprises a plurality of circumferential slots that extend partially around the circumference of the hyptotube.

18. The catheter of claim 1, where the first tubing comprises a guide wire lumen and the second tubing comprises an inflation lumen.

19. The catheter of claim 18, where the multilumenal tubing is a coaxial tube and the guide wire lumen tubing is surrounded by the inflation lumen tubing.

20. The catheter of claim 18, further comprising a guide wire extending through the guide wire lumen.

21. The catheter of claim 1, where the hypotube is made of metal or plastic.

22. The catheter of claim 1, where the tube holder is disposed within a handle.

23. The catheter of claim 22, where the first tubing exits the handle at a first location, the second tubing exits the handle at a second location, and the first location is distal to the second location.

24. The catheter of claim 1, where the catheter is a balloon catheter.

\* \* \* \* \*